United States Patent

Huser et al.

[11] Patent Number: 5,908,805
[45] Date of Patent: *Jun. 1, 1999

[54] PREPARATION OF TRANSITION METAL/PHOSPHINE CATALYSTS BY HYDROGEN REDUCTION

[75] Inventors: Marc Huser, Villeurbanne; Robert Perron, Charly, both of France

[73] Assignee: R.P. Fiber & Resin Intermediates, Courbevoie Cedex, France

[21] Appl. No.: 08/774,910

[22] Filed: Dec. 27, 1996

Related U.S. Application Data

[60] Provisional application No. 60/015,189, Apr. 12, 1996.

[30] Foreign Application Priority Data

Dec. 29, 1995 [FR] France .................................. 95 15879

[51] Int. Cl.⁶ ............................ B01J 20/34; B01J 38/10; B01J 38/68; B01J 31/00
[52] U.S. Cl. ................................. 502/53; 502/24; 502/162
[58] Field of Search ................................ 502/29, 53, 162

[56] References Cited

U.S. PATENT DOCUMENTS

| | | | |
|---|---|---|---|
| 4,087,452 | 5/1978 | Kuntz ........................................ | 260/465 |
| 4,399,312 | 8/1983 | Russell et al. ........................... | 568/454 |
| 4,473,655 | 9/1984 | Tsunoda et al. ......................... | 502/24 |
| 4,935,550 | 6/1990 | Miller et al. ............................. | 502/24 |
| 5,091,350 | 2/1992 | Cornils et al. ........................... | 502/24 |
| 5,290,743 | 3/1994 | Chang ...................................... | 502/24 |
| 5,367,107 | 11/1994 | Bahrmann et al. ..................... | 568/454 |
| 5,463,166 | 10/1995 | Lin ........................................... | 502/53 |
| 5,580,991 | 12/1996 | Sugiyama et al. ........................ | 502/24 |
| 5,599,758 | 2/1997 | Guth et al. ............................... | 502/53 |
| 5,658,843 | 8/1997 | Tsukada et al. .......................... | 502/53 |
| 5,672,798 | 9/1997 | Zhang et al. ............................. | 502/53 |
| 5,723,641 | 3/1998 | Tam et al. ................................ | 502/162 |
| 5,726,334 | 3/1998 | Beatty et al. ............................. | 502/162 |
| 5,770,684 | 6/1998 | Stewart et al. ........................... | 502/162 |

FOREIGN PATENT DOCUMENTS

| | | | |
|---|---|---|---|
| 0 269 964 | 6/1988 | European Pat. Off. ................ | 502/162 |
| 0 475 820 | 3/1992 | European Pat. Off. ................ | 502/162 |
| 0 602 463 A1 | 6/1994 | European Pat. Off. . | |
| 2 338 253 | 8/1977 | France . | |
| 2 489 308 | 3/1982 | France . | |
| 4-225841 | 8/1992 | Japan ...................................... | 502/162 |
| 2 085 874 | 5/1982 | United Kingdom ..................... | 502/24 |

OTHER PUBLICATIONS

French Search Report, Oct. 10, 1996.

*Primary Examiner*—Mark L. Bell
*Assistant Examiner*—J. Pasterczyk
*Attorney, Agent, or Firm*—Burns, Doane, Swecker & Mathis, L.L.P.

[57] ABSTRACT

Transition metal (0) or (1)/phosphine catalysts suited, e.g., for the hydrocyanation of ethylenically unsaturated compounds, are produced by reducing, via hydrogenation, aqueous solutions containing at least one transition metal compound and at least one monodentate or bidentate water-soluble phosphine, advantageously at least one phosphine having one of the following formulae (I) and/or (II):

$$P(Ar1)_a(Ar2)_b(Ar3)_c(Q1)_d(Q2)_e(Q3)_f \qquad (I)$$

$$(Ar1)_a(Ar2)_b(Ar3)_c(Q1)_d(Q2)_e P\text{-}L\text{-}P(Ar1)_g(Ar2)_h(Q1)_i(Q2)_j \qquad (II)$$

In formulas (I) and (II), Ar1, Ar2 and Ar3 may be identical or different and are each an aryl radical or a substituted aryl radical. Q1, Q2 and Q3 may be identical or different and are each an alkyl radical, a cycloalkyl radical, a substituted alkyl radical, or a substituted cycloalkyl radical.

24 Claims, No Drawings

PREPARATION OF TRANSITION METAL/PHOSPHINE CATALYSTS BY HYDROGEN REDUCTION

CROSS-REFERENCE TO COMPANION APPLICATIONS

Provisional Application No. 60/015,189, filed Apr. 12, 1996, the priority of which is hereby claimed, and copending applications Ser. No. 08/568,295, filed Dec. 6, 1995, now U.S. Pat. No. 5,679,237, and Ser. No. 08/777,392, filed concurrently herewith; each is assigned to the assignee hereof.

BACKGROUND OF THE INVENTION

TECHNICAL FIELD OF THE INVENTION

The present invention relates to a process for the preparation of transition metal/phosphine catalysts by reduction, via hydrogenation, of aqueous solutions of certain starting compounds.

SUMMARY OF THE INVENTION

The final product catalyst compounds according to this invention comprise at least one transition metal in oxidation state 0 or 1 in combination with at least one monodentate or bidentate water-soluble phosphine.

Such final product compounds can be used, for example, as catalysts in lieu of the catalysts used for the hydrocyanation of ethylenic compounds, as described in FR-A-2,338,253. Herein, these will be referred to as "catalysts," without this limiting their field of use.

Other than the synthesis of such catalysts, the present invention permits their regeneration. This is because, during actual use of these catalysts for the hydrocyanation of ethylenically unsaturated compounds, gradual oxidation of the transition metal occurs, thus resulting in the long- or short-term, at least partial deactivation of said catalysts.

Briefly, the present invention features a process for the preparation of catalysts containing at least one transition metal in oxidation state 0 or 1, combined with at least one monodentate or bidentate water-soluble phosphine, comprising hydrogenating an aqueous solution containing at least one transition metal compound and at least one monodentate or bidentate water-soluble phosphine.

DETAILED DESCRIPTION OF BEST MODE AND SPECIFIC/PREFERRED EMBODIMENTS OF THE INVENTION

More particularly according to the present invention, the water-soluble phosphine starting material is advantageously a monodentate phosphine having the general formula (I):

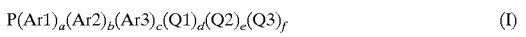

in which Ar1, Ar2 and Ar3, which may be identical or different, are each an aryl radical or aryl radical substituted by one or more substituents, such as alkyl or alkoxy radicals having from 1 to 4 carbon atoms, halogen atoms, nitrile groups, nitro groups, hydrophilic groups such as —COOM, —SO$_3$M or —PO$_3$M, wherein M is an inorganic or organic cationic residue selected from among a proton, cations derived from alkali metals or alkaline earth metals, ammonium cations N(R)$_4^+$ in which the symbols R, which may be identical or different, are each a hydrogen atom or an alkyl radical having from 1 to 4 carbon atoms, the other cations derived from metals whose arylcarboxylic acid, arylsulfonic acid or arylphosphonic acid salts are water-soluble, —N(R)$_3$ in which the symbols R, which may be identical or different, are each a hydrogen atom or an alkyl radical having from 1 to 4 carbon atoms, and/or —OH groups; a, b and c, independently, are each 0 or 1; Q1, Q2 and Q3, which may be identical or different, are each an alkyl radical, a cycloalkyl radical, or an alkyl or cycloalkyl radical substituted by one or more substituents, such as alkoxy radicals having 1 to 4 carbon atoms, halogen atoms, nitrile groups, nitro groups, hydrophilic groups such as —COOM, —SO$_3$M or —PO$_3$M, wherein M is an inorganic or organic cationic residue selected from among a proton, cations derived from alkali metals or alkaline earth metals, ammonium cations N(R)$_4^+$ in which the symbols R, which may be identical or different, are each a hydrogen atom or an alkyl radical having from 1 to 4 carbon atoms, the other cations derived from metals whose carboxylic acid, sulfonic acid or phosphonic acid salts are water-soluble, —N(R)$_3$ in which the symbols R, which may be identical or different, are each a hydrogen atom or an alkyl radical having from 1 to 4 carbon atoms, and/or —OH groups; d, e and f, independently, are each 0 or 1, with the proviso that the sum (a+b+c+d+e+f) is equal to 3.

The subject phosphine starting material can also be a bidentate phosphine having the general formula (II):

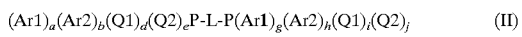

in which Ar1, Ar2, Q1 and Q2 have the formula (I) definitions indicated above;

a, b, d, e, g, h, i and j are each 0 or 1;

the sum (a+b+d+e) is equal to 2;

the sum (g+h+i+j) is equal to 2; and

L is a single valence bond or a divalent hydrocarbon radical, such as an alkylene radical, a cycloalkylene radical, an arylene radical, a radical derived from a heterocycle containing one or two oxygen, nitrogen or sulfur heteroatoms in the ring, these various cyclic radicals being bonded directly to one of the phosphorus atoms, or to the two phosphorus atoms, or being bonded to one of the phosphorus atoms or to the two via a linear or branched alkylene radical having from 1 to 4 carbon atoms, with the proviso that the ring or rings comprising the divalent radical L can be substituted by one or more substituents such as those indicated for Ar1, Ar2, Ar3, Q1, Q2 and Q3.

Exemplary metals whose carboxylic acid, sulfonic acid or phosphoric acid salts are water-soluble include lead, zinc and tin.

Herein, by the expression "water-soluble" is intended a compound which is soluble to an extent of at least 0.01 g per liter of water.

The preferred water-soluble phosphines are the phosphines of formula (I) or of formula (II) in which Ar1, Ar2 and Ar3 are phenyl groups or phenyl groups substituted by one or two substituents as described above. Q1, Q2 and Q3 are preferably alkyl radicals having from 1 to 6 carbon atoms, cycloalkyl radicals having from 5 to 8 carbon atoms, alkyl radicals having from 1 to 6 carbon atoms or cycloalkyl radicals having from 5 to 8 carbon atoms substituted by one or more substituents as defined above, and L is preferably a single valence bond, an alkylene radical having from 1 to 6 carbon atoms, a monocyclic or bicyclic cycloalkylene radical having from 4 to 12 carbon atoms, a phenylene radical, a diphenylene radical, a naphthylene radical, a dinaphthylene radical, a radical derived from a heterocycle containing one or two oxygen, nitrogen or sulfur heteroatoms in the ring, these various cyclic radicals being bonded directly to one of the phosphorus atoms, or to the two phosphorus atoms, or being bonded to one of the phosphorus atoms or to the two via a linear or branched alkylene radical having from 1 to 4 carbon atoms, with the proviso that the ring or rings comprising the divalent radical L can be substituted by one or more substituents such as an alkyl radical having from 1 to 4 carbon atoms.

Particularly preferred water-soluble phosphines are the phosphines of formula (I) or of formula (II) in which the substituent or substituents of Ar1, Ar2 and Ar3, which may be identical or different, are each alkyl or alkoxy radicals having from 1 to 2 carbon atoms, chlorine atoms, hydrophilic groups such as —COOM, —$SO_3M$ or —$PO_3M$, wherein M is an inorganic or organic cationic residue selected from among a proton, cations derived from sodium, from potassium, from calcium or from barium, ammonium, tetramethylammonium, tetraethylammonium, tetrapropylammonium and tetrabutylammonium cations, cations derived from zinc, from lead or from tin, —$N(R)_3$ in which the symbols R, which may be identical or different, are each a hydrogen atom or an alkyl radical having from 1 to 4 carbon atoms, and/or —OH groups, with the proviso that at least two of said substituents of Ar1, Ar2, Ar3, Q1, Q2 and Q3 for the phosphines of formula (I) and of Ar1, Ar2, Q1 and Q2 for the phosphines of formula (II) are hydrophilic groups as defined above.

Particularly exemplary phosphines of general formula (I) are the alkali metal or alkaline earth metal salts, the ammonium salts and the quaternary ammonium salts of (3-sulfo-4-methylphenyl)di(4-methylphenyl)phosphine; (3-sulfo-4-methoxyphenyl)di(4-methoxyphenyl)phosphine; (3-sulfo-4-chlorophenyl)di(4-chlorophenyl)phosphine; di(3-sulfophenyl)phenylphosphine; di(4-sulfophenyl) phenylphosphine; di(3-sulfo-4-methylphenyl) (4-methylphenyl)phosphine; di(3-sulfo-4-methoxyphenyl) (4-methoxyphenyl)phosphine; di(3-sulfo-4-chlorophenyl) (4-chlorophenyl)phosphine; tri(3-sulfophenyl)phosphine; tri (4-sulfophenyl)phosphine; tri(3-sulfo-4-methylphenyl) phosphine; tri(3-sulfo-4-methoxyphenyl)phosphine; tri(3-sulfo-4-chlorophenyl)phosphine; (2-sulfo-4-methylphenyl) (3-sulfo-4-methylphenyl)(3,5-disulfo-4-methylphenyl) phosphine; (3-sulfophenyl)(3-sulfo-4-chlorophenyl)(3,5-disulfo-4-chlorophenyl)phosphine; tris(hydroxymethyl) phosphine; tris(2-hydroxyethyl)phosphine; tris(3-hydroxypropyl)phosphine; tris(2-carboxymethyl) phosphine; the sodium salt of tris(3-carboxylatophenyl) phosphine; tris(3-carboxyethyl)phosphine; tris(4-trimethylammoniumphenyl)phosphine iodide; the sodium salt of tris(2-phosphonatoethyl)phosphine; bis(2-carboxyethyl)phenylphosphine; hydroxymethyl-bis(2-hydroxyethyl)phosphine; the sodium salt of tris (paraphosphonophenyl)phosphine; the sodium salt of bis (meta-sulfophenyl)-para-carboxyphenylphosphine and the sodium salt of bis(meta-sulfophenyl)-2-sulfoethylphosphine.

Particularly exemplary phosphines of general formula (II) include the sodium salt of 2,2'-bis [di(sulfonatophenyl) phosphino]-1,1'-binaphthyl; the sodium salt of 1,2-bis[di (sulfonatophenyl)phosphinomethyl]cyclobutane (CBDTS); 1,2-bis(dihydroxymethylphosphino)ethane; 1,3-bis (dihydroxymethylphosphino)propane and the sodium salt of 2,2'-bis[di(sulfonatophenyl)phosphinomethyl]-1,1'-binaphthyl.

Of course, a mixture of a plurality of these phosphines can also be used.

Certain of these water-soluble phosphines of formula (I) or (II) are commercially available.

The others can be prepared via the general or specific phosphine syntheses described in general texts such as Houben-Weyl, *Method der Organischen Chemie,* "Organische Phosphor Verbindungen," Volume 1 (1963).

Lastly, for the preparation of the water-soluble derivatives not described, it is possible, starting with phosphines containing no water-soluble substituents as defined above, to easily introduce one or more of these hydrophilic substituents. Thus, the sulfonate groups, for example, may be introduced via reaction with $SO_3$ in sulfuric acid. The carboxylate, phosphonate and quaternary ammonium groups may likewise be introduced via conventional techniques for this type of synthesis.

The preferred transition metal compounds include nickel, cobalt, iron, palladium, platinum, rhodium and iridium compounds, at least partially in an oxidation state other than 0. Water-soluble compounds or compounds that dissolve under the reaction conditions are used. The residue bonded to the metal is not essential, provided that it satisfies these conditions.

Among these compounds, the most preferred are compounds of nickel. Exemplary thereof are compounds such as nickel carboxylates (in particular acetate, formate and citrate), nickel carbonate, nickel bicarbonate, nickel borate, nickel bromide, nickel chloride, nickel iodide, nickel thiocyanate, nickel cyanide, nickel hydroxide, nickel hydrophosphite, nickel phosphite, nickel phosphate and derivatives thereof, nickel nitrate, nickel sulfate, nickel sulfite and nickel aryl and alkyl sulfonates.

It is not essential that the nickel compound itself be water-soluble. For example, nickel cyanite, which is sparingly soluble in water, dissolves well in an aqueous solution of water-soluble phosphine, in particular one which is sulfonated.

The reduction with hydrogen of the transition metal compound in the presence of at least one monodentate or bidentate water-soluble phosphine may be carried out in homogeneous phase, optionally in the presence of a homogeneous catalyst which is soluble in the reaction medium, or in heterogeneous phase in the presence of a catalyst which is insoluble in the reaction medium.

Homogeneous catalysts which are suitable are the usual catalysts for this type of catalysis, such as, for example, water-soluble phosphine complexes of rhodium, iridium, cobalt, ruthenium, nickel or palladium.

Heterogeneous catalysts which are suitable are the various metals or compounds of these metals, which are or are not deposited onto a support, and which are generally employed in catalytic hydrogenation. Among these metals, those most commonly used are the metals of Group VIII of the Periodic Table, as published in the *Handbook of Chemistry and Physics* (Weast, 5th Edition of 1970–1971). Particularly suitable Group VIII metals include platinum, palladium, ruthenium and nickel.

Supported catalysts are advantageously employed. The supports are very varied. Exemplary are the aluminas, carbon black, silicas, various metal oxides such as cerine, zirconia and titanium dioxide, and metal salts such as calcium carbonate and barium sulfate.

Exemplary preferred non-supported heterogeneous catalysts include Raney nickel and Raney cobalt. Raney nickel is most particularly preferred.

The catalytic reduction is generally carried out at a hydrogen pressure, measured at 25° C., of from 1 to 200 bar and at a temperature of from 5° C. to 200° C. Preferably, the hydrogen pressure measured at 25° C. ranges from 1 to 150 bar and the temperature from 10° C. to 120° C.

The solution of the transition metal compound to be reduced may also comprise compounds that serve to complement the catalyst prepared by the process of the invention. These compounds are, in particular, Lewis acids.

Herein, by the term "Lewis acid" is intended the usual definition thereof, i.e., electron-pair-acceptor compound.

The Lewis acids described in the text edited by G. A. Olah, *Friedel-Crafts and Related Reactions*, Volume 1, pages 191 to 197 (1963) are particularly suitable.

The Lewis acids which are useful in the reaction mixture are selected from among compounds of the elements of Groups Ib, IIb, IIIa, IIIb, IVa, IVb, Va, Vb, VIb, VIIb and VIII of the Periodic Table, as published in the *Handbook of Chemistry and Physics*, 51st Edition (1970–1971) of The Chemical Rubber Co., insofar as said compounds are at least partially soluble and stable in water or, more generally, in the aqueous solution to be treated. These compounds are typically, but without any limitation being implied, salts, in particular halides, preferably chlorides and bromides, sulfates, nitrates, sulfonates, especially trifluoromethanesulfonates, carboxylates, acetylacetonates, tetrafluoroborates and phosphates.

Exemplary such Lewis acids include zinc chloride, zinc bromide, zinc iodide, zinc trifluoromethanesulfonate, zinc acetate, zinc nitrate, zinc tetrafluoroborate, manganese chloride, manganese bromide, nickel chloride, nickel bromide, nickel cyanide, nickel acetylacetonate, cadmium chloride, cadmium bromide, stannous chloride, stannous bromide, stannous sulfate, stannous tartrate, the chlorides, bromides, sulfates, nitrates, carboxylates or trifluoromethanesulfonates of rare earth elements such as lanthanum, cerium, praseodymium, neodymium, samarium, europium, gadolinium, terbium, dysprosium, holmium, erbium, thulium, ytterbium and lutetium, cobalt chloride, ferrous chloride and yttrium chloride.

Mixtures of several of these Lewis acids can, of course, also be used.

Among the Lewis acids which are suitable, preferred are zinc chloride, zinc bromide, zinc sulfate, zinc tetrafluoroborate, stannous chloride, stannous bromide, zinc chloride/stannous chloride mixtures, nickel chloride, nickel bromide and nickel acetylacetonate.

The Lewis acid advantageously constitutes from 0 to 50 mol per mole of transition metal compound, more particularly of nickel compound, and preferably from 0 to 10 mol per mole.

A preferred embodiment of the process of the invention comprises regenerating spent catalyst, namely, a catalyst which has been used and has become at least partially inactive. Thus, a catalyst based on monodentate or bidentate water-soluble phosphine and on a transition metal in oxidation state 0 or 1, optionally also containing one or more Lewis acids, used for the hydrocyanation of butadiene and/or of pentenenitriles becomes gradually deactivated, in particular by oxidation of the transition metal. The latter, and more particularly nickel, is at least partly converted into cyanide. At the end of the hydrocyanation reaction, the aqueous phase containing, in particular, the monodentate or bidentate water-soluble phosphine and the compound of the transition metal which is at least partially in an oxidation state higher than 0, may readily be separated from the organic phase. This aqueous phase may contain variable amounts of compounds initially introduced, such as butadiene and/or pentenenitriles, or formed during the reaction, such as adiponitrile, methylglutaronitrile, ethylsuccinonitrile, pentenenitriles and methylbutenenitriles. The aqueous phase is treated as described above in order to regenerate the catalyst by reduction of the transition metal which exists in an oxidation state higher than 0.

In order to further illustrate the present invention and the advantages thereof, the following specific examples are given, it being understood that same are intended only as illustrative and in nowise limitative.

Abbreviations used:

3PN=3-pentenenitrile

ADN=adiponitrile

RC=selectivity towards a compound obtained relative to the starting compound converted t.o.=turnover=number of mmol of dinitriles formed per mmol of Ni(O) employed COD=cyclooctadiene.

EXAMPLES 1 TO 10

Reduction of $Ni(CN)_2$ on a heterogeneous catalyst

The following materials were charged into a 5 ml glass ampule:

(i) the hydrogenation catalyst (10 mol % of metal relative to the $Ni(CN)_2$ to be reduced) (mass indicated in the Table I below);

(ii) 2.4 g of an aqueous solution of $Ni(CN)_2$ (0.127 mol/kg), of sodium triphenylphosphine trisulfonate ($TPPTSNa_3$) (0.5 mol/kg) and $ZnCl_2$ (0.41 mol/kg);

(iii) 100 μl of 3-pentenenitrile (3PN) (0.42 mol/kg). (These concentrations are expressed relative to the entire reaction mixture).

The ampule was placed in an autoclave which was pressurized to 50 bar of hydrogen and heated at 100° C. for 1 hour. At the end of the test, the reactor was depressurized and the aqueous solution was analyzed by polarography. The nickel (0) concentration was calculated by the difference between the total nickel concentration and the residual nickel (II) concentration.

TABLE I

| Example | Catalyst | Mass of catalyst (mg) | [Ni(O)] (mol/kg) |
|---|---|---|---|
| Example 1 | Pd/C containing 2.5% Pd | 134.6 | 0.05 |
| Example 2 | Pd/αAl$_2$O$_3$ containing 0.5% Pd | 680 | 0.029 |
| Example 3 | Pd/γAl$_2$O$_3$ containing 5% Pd | 74.3 | 0.024 |
| Example 4 | Pd/CaCO$_3$ containing 5% Pd | 79.1 | 0.025 |
| Example 5 | Pd/BaSO$_4$ containing 5% Pd | 78.8 | 0.023 |
| Example 6 | Pt/C containing 2.5% Pt | 270 | 0.115 |
| Example 7 | Pt/αAl$_2$O$_3$ containing 0.1% Pt | 1257 | 0.026 |
| Example 8 | Pt/γAl$_2$O$_3$ containing 0.1% Pt | 1272 | 0.007 |
| Example 9 | Ru/C containing 2.55% Pd | 136 | 0.040 |
| Example 10 | Ru/γAl$_2$O$_3$ containing 5% Ru | 69 | 0.035 |

EXAMPLE 11

Reduction of $Ni(CN)_2$ on Pt/C and hydrocyanation of 3-pentenenitrile (a) Preparation of the catalyst The following materials were charged into a 125 ml glass ampule:

(i) 60 g of an aqueous solution of $Ni(CN)_2$ (0.135 mol/kg) in $TPPTSNa_3$ (0.5 mol/kg);

(ii) 3.39 g of $ZnCl_2$ (24.9 mmol of Zn);

(iii) 6.25 g of Pt/C (0.8 mmol of Pt);

(iv) 1 g of 3-pentenenitrile (12.3 mmol).

The ampule was placed in an autoclave which was pressurized to 50 bar of hydrogen and heated at 100° C. for 1 hour. At the end of the test, the reactor was decompressed and polarographic analysis of the aqueous solution indicated a nickel (0) concentration of 0.051 mol/kg (=solution 11(a)).
(b) Test using the solution 11(a) for the hydrocyanation of 3-pentenenitrile

TABLE II

| Test | Catalyst | Ni(O) (mmol) | HCN (mmol/h) | RC AND (%) | t.o. |
|---|---|---|---|---|---|
| CT1* | Ni(COD)$_2$/TPPTSNa$_3$ | 5 | 67.4 | 61 | 30 |
| CT2** | Ni(CN)$_2$(TPPTSNa$_3$)$_2$ | 0 | 67.4 | 0 | 0 |
| test | solution 11(a) | 2.15 | 28 | 67 | 25 |

Operating conditions of the hydrocyanation test: 3PN = 300 mmol, 65° C., 3 h.
CT1* = comparative test using a catalyst prepared by exchanging the COD ligands of Ni(COD)$_2$ for TPPTSNa$_3$ + ZnCl$_2$ (0.5 mol/kg).
CT2* = comparative test using a solution of Ni(CN)$_2$ (TPPTSNa$_3$)$_2$ + ZnCl$_2$ (0.5 mol/kg) not treated with hydrogen.

EXAMPLES 12 TO 16
Reduction of Ni(CN)$_2$ in homogeneous phase

The following materials were charged into a 5 ml glass ampule:
(i) 2.4 g of an aqueous solution containing Ni(CN)$_2$ (0.09 mol/kg), Ni(O) (0.03 mol/kg) and TPPTSNa$_3$ (0.5 mol/kg);
(ii) optionally, a zinc derivative (see Table III);
(iii) 25 μl of 3-pentenenitrile (0.25 mmol).

The ampule was placed in an autoclave which was pressurized to 100 bar of hydrogen and heated to 100 (duration indicated in Table III). At the end of the test, the autoclave was depressurized and the aqueous solution was analyzed by polarography. The nickel (0) concentration was calculated by the difference between the total nickel concentration and the concentration of residual nickel (II).

TABLE III

| Test | Zinc Compound | mmol of zinc | duration (h) | [Ni(O)] (mol/kg) |
|---|---|---|---|---|
| Example 12 | ZnSO$_4$ | 0.6 | 1 | 0.055 |
| Example 13 | ZnCl$_2$ | 1.1 | 1 | 0.069 |
| Example 14 | none | 0 | 0.25 | 0.052 |
| Example 15 | none | 0 | 0.5 | 0.067 |
| Example 16 | none | 0 | 1 | 0.106 |

EXAMPLE 17
Reduction of Ni(CN)$_2$ in homogeneous phase and hydrocyanation of 3-pentenenitrile
(a) Preparation of the catalyst The following materials were charged into a 125 ml glass ampule:
(i) 45 g of an aqueous solution of Ni(CN)$_2$ (0.135 mol/kg) in TPPTSNa$_3$ (0.5 mol/kg);
(ii) 15 g of an aqueous solution of Ni(O) (0.11 mol/kg) in TPPTSNa$_3$ (0.5 mol/kg);
(iii) 2 g of ZnCl$_2$ (14.7 mmol of Zn);
(iv) 0.6 g of 3-pentenenitrile (7.4 mmol).

The ampule was placed in an autoclave which was pressurized to 100 bar of hydrogen and heated at 100° C. for 1 hour. At the end of the test, the autoclave was depressurized and polarographic analysis of the aqueous solution indicated a nickel (0) concentration of 0.078 mol/kg (=solution 17(a)).
(b) Test using the solution 17(a) for the hydrocyanation of 3-pentenenitrile

TABLE IV

| Test | Catalyst | Ni(O) (mmol) | HCN (mmol/h) | RC AND (%) | t.o. |
|---|---|---|---|---|---|
| CT3* | Ni(COD)$_2$/TPPTSNa$_3$ | 5 | 67.4 | 61 | 30 |
| CE4** | Ni(CN)$_2$(TPPTSNa$_3$)$_2$ | 0 | 67.4 | 0 | 0 |
| test | solution 17(a) | 3.3 | 42.9 | 67 | 28 |

Operating conditions of the hydrocyanation test: 3PN = 300 mmol, 65° C., 3h.
CT3* = comparative test using a catalyst prepared by exchanging the COD ligands of Ni(COD)$_2$ for TPPTSNa$_3$ + ZnCl$_2$ (0.5 mol/kg).
CT4* = comparative test using a solution of Ni(CN)$_2$ (TPPTSNa$_3$)$_2$+ZnCl$_2$ (0.5 mol/kg) not treated with hydrogen.

EXAMPLES 18 TO 20
Reduction of Ni(CN)$_2$ on a heterogeneous catalyst

The following materials were charged into a 5 ml glass ampule:
(i) the hydrogenation catalyst (mass indicated in Table V below);
(ii) 2.2 g of an aqueous solution of Ni(CN)$_2$ (0.12 to 0.13 mol/kg), sodium triphenylphosphine trisulfonate (TPPTSNa$_3$) (0.5 mol/kg) and ZnCl$_2$ (0.100 g);
(iii) 100 μl of 3-pentenenitrile (3PN) (0.42 mol/kg).
(These concentrations are expressed relative to the entire reaction mixture).

The ampule was placed in an autoclave which was pressurized to 100 bar of hydrogen and stirred at room temperature (about 25° C.) for 1 hour. At the end of the test, the reactor was depressurized and the aqueous solution was analyzed by polarography. The nickel (0) concentration was calculated by the difference between the total nickel concentration and the concentration of residual nickel (II).

No precipitate of nickel was observed and in each test the amount of total nickel assayed corresponded, within the accuracy limits of the analysis, to the amount introduced at the start of the test.

TABLE V

| Example | Catalyst | Total Ni assayed (mol/kg) | Ni(O) assayed (mol/kg) |
|---|---|---|---|
| Example 18 | Pt/C at 5% by weight (0.234 g) | 0.130 | 0.063 |
| Example 19 | Pt/C at 5% by weight (0.269 g) | 0.135 | 0.074 |
| Example 20 | Pt/C at 0.88% by weight (0.401 g) | 0.119 | 0.053 |

EXAMPLES 21 TO 25
Reduction of Ni(CN)$_2$ on a heterogeneous catalyst

The following materials were charged into a 5 ml glass ampule:
(i) the hydrogenation catalyst (nature and mass indicated in Table VI below);
(ii) 2.2 g of an aqueous solution of Ni(CN)$_2$ (0.112 mol/kg) and sodium triphenylphosphine trisulfonate (TPPTSNa$_3$) (0.5 mol/kg);
(iii) 130 to 150 μl of 3-pentenenitrile (3PN). (These concentrations are expressed relative to the entire reaction mixture).

The ampule was placed in an autoclave which was pressurized to 100 bar of hydrogen and stirred at different temperatures (indicated in Table VI below under the abbreviation TIC) for different durations. At the end of the test, the reactor was depressurized and the aqueous solution was analyzed by polarography. The nickel (0) concentration was calculated by the difference between the total nickel concentration and the concentration of residual nickel (II).

No nickel precipitate was observed (except a very slight precipitate in Example 23 corresponding to less than 0.003 mol/kg) and in each test the amount of total nickel assayed corresponded, within the accuracy limits of the analysis, to the amount introduced at the start of the test.

TABLE VI

| Example | Catalyst | T° C. | Duration | Total Ni assayed (mol/kg) | Ni(O) assayed (mol/kg) |
|---------|----------|-------|----------|---------------------------|------------------------|
| Example 21 | Pt/C at 5% by weight (0.26 g) | 65 | 1 h, 30 min | 0.113 | 0.091 |
| Example 22 | Pt/C at 5% by weight (0.23 g) | 25 | 4 h | 0.113 | 0.089 |
| Example 23 | Pt/alumina at 0.5% by weight (0.99 g) | 25 | 4 h | 0.109 | 0.044 |
| Example 24 | wet Raney nickel (0.09 g) | 40 | 1 h, 30 min | 0.108 | 0.103 |
| Example 25 | wet Raney nickel (0.06 g) | 65 | 1 h, 30 min | 0.109 | 0.099 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a catalyst which comprises at least one transition metal in an oxidation state of 0 or 1 and at least one monodentate or bidentate water-soluble phosphine, comprising reducing, with a reducing agent consisting essentially of hydrogen, an aqueous solution comprising at least one starting transition metal compound and at least one starting monodentate or bidentate water-soluble phosphine to obtain said catalyst.

2. The process as defined by claim 1, said at least one starting monodentate water-soluble phosphine having the formula (I):

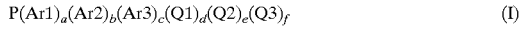

$$P(Ar1)_a(Ar2)_b(Ar3)_c(Q1)_d(Q2)_e(Q3)_f \quad (I)$$

in which Ar1, Ar2 and Ar3, which may be identical or different, are each an aryl radical or aryl radical substituted by one or more substituents selected from the group consisting of:

alkyl radicals having from 1 to 4 carbon atoms,
alkoxy radicals having from 1 to 4 carbon atoms,
halogen atoms,
nitrile groups,
nitro groups,
the hydrophilic groups —COOM, —SO₃M and —PO₃M, wherein M is an inorganic or organic cationic residue selected from the group consisting of:
 a proton,
 alkali metals,
 alkaline earth metals,
 ammonium cations $N(R)_4^+$ in which the symbols R, which may be identical or different, are each a hydrogen atom, or an alkyl radical having from 1 to 4 carbon atoms, and
 metals whose arylcarboxylic acid, arylsulfonic acid or arylphosphonic acid salts are water-soluble,
—N(R)₃ in which the symbols R, which may be identical or different, are each a hydrogen atom or an alkyl radical having from 1 to 4 carbon atoms, and
—OH groups;
a, b and c, independently, are each 0 or 1; Q1, Q2 and Q3, which may be identical or different, are each an alkyl radical, a cycloalkyl radical, or an alkyl or cycloalkyl radical substituted by one or more substituents selected from the group consisting of:
alkoxy radicals having from 1 to 4 carbon atoms,
halogen atoms,
nitrile groups,
nitro groups,
the hydrophilic groups —COOM, —SO₃M and —PO₃M, wherein M is an inorganic or organic cationic residue selected from the group consisting of:
 a proton,
 alkali metals,
 alkaline earth metals,
 ammonium cations $N(R)_4^+$ in which the symbols R, which may be identical or different, are each a hydrogen atom or an alkyl radical having from 1 to 4 carbon atoms, and
 metals whose carboxylic acid, sulfonic acid or phosphonic acid salts are water-soluble,
—N(R)₃ in which the symbols R, which may be identical or different, are each a hydrogen atom or an alkyl radical having from 1 to 4 carbon atoms, and
—OH groups;
and d, e and f, independently, are each 0 or 1, with the proviso that the sum (a+b+c+d+e+f) is equal to 3.

3. The process as defined by claim 1, said at least one starting bidentate water-soluble phosphine having the formula (II):

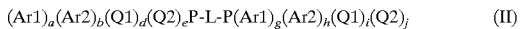

$$(Ar1)_a(Ar2)_b(Q1)_d(Q2)_e P\text{-}L\text{-}P(Ar1)_g(Ar2)_h(Q1)_i(Q2)_j \quad (II)$$

in which Ar1 and Ar2, which may be identical or different, are each an aryl radical or aryl radical substituted by one or more substituents selected from the group consisting of:

alkyl radicals having from 1 to 4 carbon atoms,
alkoxy radicals having from 1 to 4 carbon atoms,
halogen atoms,
nitrile groups,
nitro groups,
the hydrophilic groups —COOM, —SO₃M and —PO₃M, wherein M is an inorganic or organic cationic residue selected from the group consisting of:
 a proton,
 alkali metals,
 alkaline earth metals,
 ammonium cations $N(R)R_4^+$ in which the symbols R, which may be identical or different, are each a hydrogen atom or an alkyl radical having from 1 to 4 carbon atoms, and
 metals whose arylcarboxylic acid, arylsulfonic acid or arylphosphonic acid salts are water-soluble,
—N(R)₃ in which the symbols R, which may be identical or different, are each a hydrogen atom or an alkyl radical having from 1 to 4 carbon atoms, and
—OH groups;
Q1 and Q2, which may be identical or different, are each an alkyl radical, a cycloalkyl radical, or an alkyl or cycloalkyl radical substituted by one or more substituents selected from the group consisting of:
alkoxy radicals having from 1 to 4 carbon atoms,
halogen atoms,
nitrile groups,
nitro groups,
the hydrophilic groups —COOM, —SO$_3$M and —PO$_3$M, wherein M is an inorganic or organic cationic residue selected from the group consisting of:
a proton,
alkali metals,
alkaline earth metals,
ammonium cations N(R)R$_4^+$ in which the symbols R, which may be identical or different, are each a hydrogen atom or an alkyl radical having from 1 to 4 carbon atoms, and
metals whose carboxylic acid, sulfonic acid or phosphoric acid salts are water-soluble,
—N(R)$_3$ in which the symbols R, which may be identical or different, are each a hydrogen atom or an alkyl radical having from 1 to 4 carbon atoms, and
—OH groups;
a, b, d, e, h, i and j, independently, are each 0 or 1; the sum (a+b+d+e) is equal to 2; the sum (g+h+i+j) is equal to 2;
and L is a single valence bond or a divalent hydrocarbon radical selected from the group consisting of:
an alkylene radical,
a cycloalkylene radical,
an arylene radical, and
a heterocycle radical containing one or two oxygen, nitrogen or sulfur heteroatoms in the ring,
wherein the cyclic radicals are bonded directly to one of the phosphorus atoms, or to the two phosphorus atoms, or bonded to one of the phosphorus atoms or to the two phosphorous atoms via a linear or branched alkylene radical having from 1 to 4 carbon atoms, with the proviso that the ring or rings comprising the divalent radical L can be substituted by one or more of the substituents indicated for Ar1, Ar2, Q1 and Q2.

4. The process as defined by claim 1, said at least one starting transition metal compound comprising a compound of nickel, cobalt, iron, palladium, platinum, rhodium or iridium.

5. The process as defined by claim 4, said at least one starting transition metal compound comprising a nickel carboxylate, nickel carbonate, nickel bicarbonate, nickel borate, nickel bromide, nickel chloride, nickel iodide, nickel thiocyanate, nickel cyanide, nickel hydroxide, nickel hydrophosphite, nickel phosphite, nickel phosphate, nickel nitrate, nickel sulfate, nickel sulfite or a nickel aryl or alkyl sulfonate.

6. The process as defined by claim 1, said reducing being carried out in a homogeneous medium.

7. The process as defined by claim 6, said reducing being carried out in the presence of a catalytically effective amount of an additional catalyst which is soluble in said aqueous solution.

8. The process as defined by claim 7, said additional catalyst comprising a water-soluble phosphine complex of rhodium, iridium, cobalt, ruthenium, nickel or palladium.

9. The process as defined by claim 1, said reducing being carried out in the presence of a catalytically effective amount of an additional catalyst which is insoluble in said aqueous solution.

10. The process as defined by claim 9, said additional catalyst comprising a metal of Group VIII of the Periodic Table or compound thereof.

11. The process as defined by claim 9, said additional catalyst comprising platinum, palladium, ruthenium or nickel.

12. The process as defined by claim 2, wherein in formula (I) Ar1 Ar2 and Ar3 are phenyl groups or phenyl groups bearing one or two of said substituents; and Q1, Q2 and Q3 are each an alkyl radical having from 1 to 6 carbon atoms, a cycloalkyl radical having from 5 to 8 carbon atoms, an alkyl radical having from 1 to 6 carbon atoms or a cycloalkyl radical having from 5 to 8 carbon atoms bearing one or more of said substituents.

13. The process as defined by claim 3, wherein in formula (II) An1 and Ar2 are phenyl groups or phenyl groups bearing one or two of said substituents; Q1 and Q2 are each an alkyl radical having from 1 to 6 carbon atoms, a cycloalkyl radical having from 5 to 8 carbon atoms, an alkyl radical having from 1 to 6 carbon atoms or a cycloalkyl radical having from 5 to 8 carbon atoms bearing one or more of said substituents; and L is a single valence bond, an alkylene radical having from 1 to 6 carbon atoms, a monocyclic or bicyclic cycloalkylene radical having from 4 to 12 carbon atoms, a phenylene radical, a diphenylene radical, a naphthylene radical, a dinaphthylene radical, a heterocycle radical containing one or two oxygen, nitrogen or sulfur heteroatoms in the ring, said cyclic radicals being bonded directly to one of the phosphorus atoms, or to the two phosphorus atoms, or being bonded to one of the phosphorus atoms or to the two via a linear or branched alkylene radical having from 1 to 4 carbon atoms, with the proviso that the ring or rings comprising the divalent radical L can be substituted by one or more of said substituents.

14. The process as defined by claim 2, wherein in formula (I), one or more of Ar1, Ar2, Ar3, Q1, Q2 and Q3 are substituted, said substituent or substituents, which may be identical or different, is/are each:
an alkyl radical having from 1 to 2 carbon atoms,
alkoxy radical having from 1 to 2 carbon atoms,
a chlorine atom,
a hydrophilic group —COOM, —SO$_3$M or —PO$_3$M, wherein M is an inorganic or organic cationic residue selected from the group consisting of a proton, sodium, potassium, calcium, barium, ammonium, tetramethylammonium, tetraethylammonium, tetrapropylammonium, tetrabutylammonium, zinc, lead and tin,
—N(R)$_3$ in which the symbols R, which may be identical or different, are each a hydrogen atom or an alkyl radical having from 1 to 4 carbon atoms, or
—OH groups,
with the proviso that at least two of said substituents of Ar1, Ar2, Ar3, Q1, Q2, and Q3 are said hydrophilic groups.

15. The process as defined by claim 3, wherein in formula (I), one or more of Ar1, Ar2, Q1 and Q2 are substituted, said substituent or substituents, which may be identical or different, is/are each:
an alkyl radical having from 1 to 2 carbon atoms,
alkoxy radical having from 1 to 2 carbon atoms,
a chlorine atom,
a hydrophilic group —COOM, —SO$_3$M or —PO$_3$M, wherein M is an inorganic or organic cationic residue selected from the group consisting of a proton, sodium, potassium, calcium, barium, ammonium, tetramethylammonium, tetraethylammonium, tetrapropylammonium, tetrabutylammonium, zinc, lead and tin, —N(R)$_3$ in which the symbols R, which may be identical or different, are each a hydrogen atom or an alkyl radical having from 1 to 4 carbon atoms, and —OH groups, with the proviso that at least two of said substituents of Ar1, Ar2, Q1 and Q2 are said hydrophilic groups.

16. The process as defined by claim 1, wherein said at least one starting monodentate or bidentate water-soluble phosphine is an alkali metal or alkaline earth metal salt, an ammonium salt or a quaternary ammonium salt of (3-sulfo-4-methylphenyl)di(4-methylphenyl)phosphine; (3-sulfo-4-methoxyphenyl)di(4-methoxyphenyl)phosphine; (3-sulfo-4-chlorophenyl)di(4-chlorophenyl)phosphine; di(3-sulfophenyl)phenylphosphine; di(4-sulfophenyl)phenylphosphine; di(3-sulfo-4-methylphenyl)(4-methylphenyl)phosphine; di(3-sulfo-4-methoxyphenyl)(4-methoxyphenyl)phosphine; di(3-sulfo-4-chlorophenyl)(4-chlorophenyl)phosphine; tri(3-sulfophenyl)phosphine; tri(4-sulfophenyl)phosphine; tri(3-sulfo-4-methylphenyl)phosphine; tri(3-sulfo-4-methoxyphenyl)phosphine; tri(3-sulfo-4-chlorophenyl)phosphine; (2-sulfo-4-methylphenyl)(3-sulfo-4-methylphenyl)(3,5-disulfo-4-methylphenyl)phosphine; (3-sulfophenyl)(3-sulfo-4-chlorophenyl)(3,5-disulfo-4-chlorophenyl)phosphine; tris(hydroxymethyl)phosphine; tris(2-hydroxyethyl)phosphine; tris(3-hydroxypropyl)phosphine; tris(2-carboxymethyl)phosphine; the sodium salt of tris(3-carboxylatophenyl)phosphine; tris(3-carboxyethyl)phosphine; tris(4-trimethylammoniumphenyl)phosphine iodide; the sodium salt of tris(2-phosphonatoethyl)phosphine; bis(2-carboxyethyl)phenylphosphine; hydroxymethyl-bis(2-hydroxyethyl)phosphine; the sodium salt of tris(para-phosphonophenyl)phosphine; the sodium salt of bis(meta-sulfophenyl)-para-carboxyphenylphosphine or the sodium salt of bis(meta-sulfophenyl)-2-sulfoethylphosphine.

17. The process as defined by claim 1, wherein said at least one starting monodentate or bidentate water-soluble phosphine is the sodium salt of 2,2'-bis(di(sulfonatophenyl)phosphino)-1,1'-binaphthyl; the sodium salt of 1,2-bis(di(sulfonatophenyl)phosphinomethyl)cyclobutane (CBDTS); 1,2-bis(dihydroxymethylphosphino)ethane; 1,3-bis(dihydroxymethylphosphino)propane or the sodium salt of 2,2'-bis(di(sulfonatophenyl)phosphinomethyl)-1,1'-binaphthyl.

18. The process as defined by claim 1, said aqueous solution comprising at least one Lewis acid selected from among compounds of the elements of Groups Ib, IIb, IIIa, IIIb, IVa, IVb, Va, Vb, VIb, VIIb and VIII of the Periodic Table.

19. The process as defined by claim 18, said at least one Lewis acid comprising zinc chloride, zinc bromide, zinc iodide, zinc trifluoromethanesulfonate, zinc acetate, zinc nitrate, zinc tetrafluoroborate, manganese chloride, manganese bromide, nickel chloride, nickel bromide, nickel cyanide, nickel acetylacetonate, cadmium chloride, cadmium bromide, stannous chloride, stannous bromide, stannous sulfate, stannous tartrate, the chlorides, bromides, sulfates, nitrates, carboxylates or trifluoromethanesulfonates of lanthanum, cerium, praseodymium, neodymium, samarium, europium, gadolinium, terbium, dysprosium, holmium, erbium, thulium, ytterbium or lutetium, cobalt chloride, ferrous chloride or yttrium chloride.

20. The process as defined by claim 1, said aqueous solution comprising a deactivated catalyst to be regenerated, based on at least one monodentate or bidentate water-soluble phosphine and at least one transition metal.

21. The process as defined by claim 1, carried out at a hydrogen pressure, measured at 25° C., ranging from 1 to 200 bar and at a temperature ranging from 5° C. to 200° C.

22. The catalyst made by the process as defined by claim 1.

23. A process for the preparation of a catalyst which comprises cobalt, nickel or iron in an oxidation state of 0 or 1 and at least one monodentate or bidentate water-soluble phosphine, said process comprising reducing, with hydrogen, an aqueous solution comprising a starting compound which is a cobalt compound, a nickel compound or an iron compound and at least one starting monodentate or bidentate water-soluble phosphine to obtain said catalyst.

24. The process of claim 23, wherein said starting compound is a nickel compound.

* * * * *